(12) United States Patent
Hanson et al.

(10) Patent No.: US 8,821,478 B2
(45) Date of Patent: Sep. 2, 2014

(54) CATHETER WITH VARIABLE STIFFNESS

(75) Inventors: Cass A. Hanson, St. Paul, MN (US);
Daniel T. Quillin, Eden Prairie, MN (US); Barry L. Rudman, Forest Lake, MN (US); Ajay Gupta, Little Canada, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 239 days.

(21) Appl. No.: 13/411,309

(22) Filed: Mar. 2, 2012

(65) Prior Publication Data

US 2012/0253193 A1    Oct. 4, 2012

Related U.S. Application Data

(60) Provisional application No. 61/449,271, filed on Mar. 4, 2011.

(51) Int. Cl.
*A61M 25/00* (2006.01)

(52) U.S. Cl.
USPC .............................................. 604/525; 606/2

(58) Field of Classification Search
CPC .......... A61B 1/00078; A61M 25/0155; A61M 2025/0063
USPC ................. 600/435; 604/96.01, 97.01, 99.01, 604/102.02, 103.06, 523; 606/2
See application file for complete search history.

(56) References Cited

U.S. PATENT DOCUMENTS

| | | | |
|---|---|---|---|
| 3,472,230 A | 10/1969 | Fogarty | |
| 3,592,186 A | 7/1971 | Oster | |
| 3,683,904 A | 8/1972 | Forster | |
| 3,889,657 A | 6/1975 | Baumgarten | |
| 3,952,747 A | 4/1976 | Kimmell, Jr. | |
| 3,996,938 A | 12/1976 | Clark, III | |
| 4,046,150 A | 9/1977 | Schwartz et al. | |

(Continued)

FOREIGN PATENT DOCUMENTS

| | | |
|---|---|---|
| DE | 2821048 C2 | 7/1980 |
| DE | 3417738 A1 | 11/1985 |

(Continued)

OTHER PUBLICATIONS

"Atherosclerotic Disease of the Aortic Arch as a Risk Factor of Recurrent Ischemic Stroke", The New England Journal of Medicine, 334(18):1216-1221, May 1996.

(Continued)

*Primary Examiner* — Nicholas Lucchesi
*Assistant Examiner* — Gerald Landry, III
(74) *Attorney, Agent, or Firm* — Seager, Tufte & Wickhem, LLC (57) ABSTRACT

Medical devices and methods for making and using medical devices are disclosed. An example medical device may include an elongate inner member having a guidewire lumen extending therethrough. An outer member may be disposed about the inner member. An inflation lumen may be formed between the inner member and the outer member. The medical device may be configured to have a first stiffness when the inflation lumen is free of inflation media and a second stiffness different from the first stiffness when inflation media is disposed within the inflation lumen. In addition, the inner member may include a collapsible region that is configured to deflect radially inward when inflation media is disposed within the inflation lumen.

13 Claims, 9 Drawing Sheets

(56) References Cited

U.S. PATENT DOCUMENTS

| | | | |
|---|---|---|---|
| 4,425,908 A | 1/1984 | Simon |
| 4,447,227 A | 5/1984 | Kotsanis |
| 4,580,568 A | 4/1986 | Gianturco |
| 4,590,938 A | 5/1986 | Segura et al. |
| 4,619,246 A | 10/1986 | Molgaard-Nielsen et al. |
| 4,631,052 A | 12/1986 | Kensey |
| 4,643,184 A | 2/1987 | Mobin-Uddin |
| 4,650,466 A | 3/1987 | Luther |
| 4,662,885 A | 5/1987 | DiPisa, Jr. |
| 4,705,517 A | 11/1987 | DiPisa, Jr. |
| 4,706,671 A | 11/1987 | Weinrib |
| 4,723,549 A | 2/1988 | Wholey et al. |
| 4,728,319 A | 3/1988 | Masch |
| 4,733,665 A | 3/1988 | Palmaz |
| 4,790,812 A | 12/1988 | Hawkins, Jr. et al. |
| 4,790,813 A | 12/1988 | Kensey |
| 4,794,928 A | 1/1989 | Kletschka |
| 4,794,931 A | 1/1989 | Yock |
| 4,800,882 A | 1/1989 | Gianturco |
| 4,807,626 A | 2/1989 | McGirr |
| 4,842,579 A | 6/1989 | Shiber |
| 4,857,045 A | 8/1989 | Rydell |
| 4,857,046 A | 8/1989 | Stevens et al. |
| 4,867,157 A | 9/1989 | McGurk-Burleson et al. |
| 4,873,978 A | 10/1989 | Ginsburg |
| 4,898,575 A | 2/1990 | Fischell et al. |
| 4,907,336 A | 3/1990 | Gianturco |
| 4,921,478 A | 5/1990 | Solano et al. |
| 4,921,484 A | 5/1990 | Hillstead |
| 4,926,858 A | 5/1990 | Gifford, III et al. |
| 4,932,959 A | 6/1990 | Horzewski et al. |
| 4,950,277 A | 8/1990 | Farr |
| 4,955,895 A | 9/1990 | Sugiyama et al. |
| 4,957,482 A | 9/1990 | Shiber |
| 4,969,891 A | 11/1990 | Gewertz |
| 4,979,951 A | 12/1990 | Simpson |
| 4,986,807 A | 1/1991 | Farr |
| 4,998,539 A | 3/1991 | Delsanti |
| 5,002,560 A | 3/1991 | Machold et al. |
| RE33,569 E | 4/1991 | Gifford, III et al. |
| 5,007,896 A | 4/1991 | Shiber |
| 5,007,917 A | 4/1991 | Evans |
| 5,011,488 A | 4/1991 | Ginsburg |
| 5,019,088 A | 5/1991 | Farr |
| 5,041,126 A | 8/1991 | Gianturco |
| 5,053,008 A | 10/1991 | Bajaj |
| 5,053,044 A | 10/1991 | Mueller et al. |
| 5,071,407 A | 12/1991 | Termin et al. |
| 5,071,425 A | 12/1991 | Gifford, III et al. |
| 5,085,662 A | 2/1992 | Willard |
| 5,087,265 A | 2/1992 | Summers |
| 5,100,423 A | 3/1992 | Fearnot |
| 5,100,424 A | 3/1992 | Jang et al. |
| 5,100,425 A | 3/1992 | Fischell et al. |
| 5,102,415 A | 4/1992 | Guenther et al. |
| 5,104,399 A | 4/1992 | Lazarus |
| 5,106,376 A | 4/1992 | Mononen et al. |
| 5,108,419 A | 4/1992 | Reger et al. |
| 5,116,305 A | 5/1992 | Milder et al. |
| 5,133,733 A | 7/1992 | Rasmussen et al. |
| 5,135,531 A | 8/1992 | Shiber |
| 5,152,771 A | 10/1992 | Sabbaghian et al. |
| 5,152,777 A | 10/1992 | Goldberg et al. |
| 5,160,342 A | 11/1992 | Reger et al. |
| 5,171,233 A | 12/1992 | Amplatz et al. |
| 5,190,546 A | 3/1993 | Jervis |
| 5,195,955 A | 3/1993 | Don Michael |
| 5,217,434 A | 6/1993 | Arney |
| 5,224,953 A | 7/1993 | Morgentaler |
| 5,231,989 A | 8/1993 | Middleman et al. |
| 5,238,004 A | 8/1993 | Sahatjian et al. |
| 5,306,286 A | 4/1994 | Stack et al. |
| 5,314,444 A | 5/1994 | Gianturco |
| 5,314,472 A | 5/1994 | Fontaine |
| 5,318,576 A | 6/1994 | Plassche, Jr. et al. |
| 5,324,259 A | 6/1994 | Taylor et al. |
| 5,329,942 A | 7/1994 | Gunther et al. |
| 5,330,484 A | 7/1994 | Gunther et al. |
| 5,330,500 A | 7/1994 | Song |
| 5,350,398 A | 9/1994 | Pavcnik et al. |
| 5,354,310 A | 10/1994 | Garnic et al. |
| 5,356,423 A | 10/1994 | Tihon et al. |
| 5,366,464 A | 11/1994 | Belknap |
| 5,366,473 A | 11/1994 | Winston et al. |
| 5,370,657 A | 12/1994 | Irie |
| 5,370,683 A | 12/1994 | Fontaine |
| 5,376,100 A | 12/1994 | Lefebvre |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,349 A | 3/1995 | Quiachon et al. |
| 5,397,345 A | 3/1995 | Lazerus |
| 5,405,377 A | 4/1995 | Cragg |
| 5,409,454 A | 4/1995 | Fischell et al. |
| 5,415,630 A | 5/1995 | Gory et al. |
| 5,419,774 A | 5/1995 | Willard et al. |
| 5,421,832 A | 6/1995 | Lefebvre |
| 5,423,742 A | 6/1995 | Theron |
| 5,423,885 A | 6/1995 | Williams |
| 5,425,765 A | 6/1995 | Tiefenbrun et al. |
| 5,443,498 A | 8/1995 | Fontaine |
| 5,449,372 A | 9/1995 | Schmaltz et al. |
| 5,456,667 A | 10/1995 | Ham et al. |
| 5,462,529 A | 10/1995 | Simpson et al. |
| 5,476,104 A | 12/1995 | Sheahon |
| 5,484,418 A | 1/1996 | Quiachon et al. |
| 5,499,973 A | 3/1996 | Saab |
| 5,507,767 A | 4/1996 | Maeda et al. |
| 5,512,044 A | 4/1996 | Duer |
| 5,527,354 A | 6/1996 | Fontaine et al. |
| 5,531,689 A * | 7/1996 | Burns et al. ............ 604/99.04 |
| 5,536,242 A | 7/1996 | Willard et al. |
| 5,540,707 A | 7/1996 | Ressemann et al. |
| 5,549,626 A | 8/1996 | Miller et al. |
| 5,562,724 A | 10/1996 | Vorwerk et al. |
| 5,569,274 A | 10/1996 | Rapacki et al. |
| 5,569,275 A | 10/1996 | Kotula et al. |
| 5,634,897 A | 6/1997 | Dance et al. |
| 5,658,296 A | 8/1997 | Bates et al. |
| 5,662,671 A | 9/1997 | Barbut et al. |
| 5,669,933 A | 9/1997 | Simon et al. |
| 5,695,519 A | 12/1997 | Summers et al. |
| 5,709,704 A | 1/1998 | Nott et al. |
| 5,720,764 A | 2/1998 | Naderlinger |
| 5,728,066 A | 3/1998 | Daneshvar |
| 5,730,734 A | 3/1998 | Adams et al. |
| 5,746,758 A | 5/1998 | Nordgren et al. |
| 5,749,848 A | 5/1998 | Jang et al. |
| 5,749,849 A * | 5/1998 | Engelson ............ 604/525 |
| 5,769,816 A | 6/1998 | Barbut et al. |
| 5,772,609 A | 6/1998 | Nguyen et al. |
| 5,779,716 A | 7/1998 | Cano et al. |
| 5,792,300 A | 8/1998 | Inderbitzen et al. |
| 5,795,322 A | 8/1998 | Boudewijn |
| 5,797,952 A | 8/1998 | Klein |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,817,102 A | 10/1998 | Johnson et al. |
| 5,827,324 A | 10/1998 | Cassell et al. |
| 5,833,604 A | 11/1998 | Houser et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,879,324 A * | 3/1999 | von Hoffmann ............ 604/500 |
| 5,891,112 A | 4/1999 | Samson |
| 5,893,867 A | 4/1999 | Bagaoisan et al. |
| 5,895,399 A | 4/1999 | Barbut et al. |
| 5,897,536 A | 4/1999 | Nap et al. |
| 5,902,263 A | 5/1999 | Patterson et al. |

(56) References Cited

U.S. PATENT DOCUMENTS

| | | | |
|---|---|---|---|
| 5,906,618 A | 5/1999 | Larson, III | |
| 5,908,395 A | 6/1999 | Stalker et al. | |
| 5,908,435 A | 6/1999 | Samuels | |
| 5,910,154 A | 6/1999 | Tsugita et al. | |
| 5,911,734 A | 6/1999 | Tsugita et al. | |
| 5,916,193 A | 6/1999 | Stevens et al. | |
| 5,919,162 A | 7/1999 | Burns | |
| 5,925,016 A | 7/1999 | Chornenky et al. | |
| 5,925,060 A | 7/1999 | Forber | |
| 5,925,062 A | 7/1999 | Purdy | |
| 5,925,063 A | 7/1999 | Khosravi | |
| 5,928,203 A | 7/1999 | Davey et al. | |
| 5,928,218 A | 7/1999 | Gelbfish | |
| 5,934,284 A | 8/1999 | Plaia et al. | |
| 5,935,139 A | 8/1999 | Bates | |
| 5,938,645 A | 8/1999 | Gordon | |
| 5,941,869 A | 8/1999 | Patterson et al. | |
| 5,941,896 A | 8/1999 | Kerr | |
| 5,947,995 A | 9/1999 | Samuels | |
| 5,951,585 A | 9/1999 | Cathcart et al. | |
| 5,954,745 A | 9/1999 | Gertler et al. | |
| 5,976,172 A | 11/1999 | Homsma et al. | |
| 5,989,210 A | 11/1999 | Morris et al. | |
| 5,989,271 A | 11/1999 | Bonnette et al. | |
| 5,989,281 A | 11/1999 | Barbut et al. | |
| 5,993,469 A | 11/1999 | Mckenzie et al. | |
| 5,997,557 A | 12/1999 | Barbut et al. | |
| 6,001,118 A | 12/1999 | Daniel et al. | |
| 6,007,557 A | 12/1999 | Ambrisco et al. | |
| 6,010,522 A | 1/2000 | Barbut et al. | |
| 6,013,085 A | 1/2000 | Howard | |
| 6,027,520 A | 2/2000 | Tsugita et al. | |
| 6,051,014 A | 4/2000 | Jang | |
| 6,053,932 A | 4/2000 | Daniel et al. | |
| 6,059,814 A | 5/2000 | Ladd | |
| 6,068,645 A | 5/2000 | Tu | |
| 6,086,605 A | 7/2000 | Barbut et al. | |
| 6,129,739 A | 10/2000 | Khosravi | |
| 6,139,510 A | 10/2000 | Palermo | |
| 6,142,987 A | 11/2000 | Tsugita | |
| 6,152,946 A | 11/2000 | Broome et al. | |
| 6,165,200 A | 12/2000 | Tsugita et al. | |
| 6,168,579 B1 | 1/2001 | Tsugita | |
| 6,171,327 B1 | 1/2001 | Daniel et al. | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,203,561 B1 | 3/2001 | Ramee et al. | |
| 6,214,026 B1 | 4/2001 | Lepak et al. | |
| 6,231,543 B1 | 5/2001 | Hegde et al. | |
| 6,231,545 B1* | 5/2001 | Kriesel et al. | 604/132 |
| 6,368,338 B1 | 4/2002 | Konya et al. | |
| 6,398,798 B2 | 6/2002 | Selmon et al. | |
| 6,428,552 B1 | 8/2002 | Sparks | |
| 6,500,166 B1 | 12/2002 | Zadno Azizi et al. | |
| 6,506,178 B1 | 1/2003 | Schubart et al. | |
| 6,508,803 B1 | 1/2003 | Horikawa et al. | |
| 6,508,825 B1 | 1/2003 | Selmon et al. | |
| 6,511,458 B2 | 1/2003 | Milo et al. | |
| 6,514,217 B1 | 2/2003 | Selmon et al. | |
| 6,533,751 B2 | 3/2003 | Cragg et al. | |
| 6,533,753 B1 | 3/2003 | Haarstad et al. | |
| 6,544,276 B1 | 4/2003 | Azizi | |
| 6,547,768 B2 | 4/2003 | Trotta | |
| 6,579,302 B2 | 6/2003 | Duerig et al. | |
| 6,605,062 B1 | 8/2003 | Hurley et al. | |
| 6,786,886 B2* | 9/2004 | Miller et al. | 604/96.01 |
| 6,837,867 B2 | 1/2005 | Kortelling | |
| 7,695,465 B2* | 4/2010 | Tomaschko et al. | 604/525 |
| 8,292,827 B2* | 10/2012 | Musbach et al. | 600/585 |
| 2008/0015541 A1* | 1/2008 | Rosenbluth et al. | 604/509 |
| 2010/0125244 A1* | 5/2010 | Mcandrew | 604/98.01 |
| 2010/0168007 A1* | 7/2010 | Cruise et al. | 514/12 |

FOREIGN PATENT DOCUMENTS

| | | |
|---|---|---|
| DE | 4030998 A1 | 4/1998 |
| EP | 0200688 A1 | 11/1986 |
| EP | 0293605 A1 | 12/1988 |
| EP | 0411118 A1 | 2/1991 |
| EP | 0427429 A2 | 5/1991 |
| EP | 0437121 B1 | 7/1991 |
| EP | 0472334 A1 | 2/1992 |
| EP | 0472368 A2 | 2/1992 |
| EP | 0517075 A1 | 12/1992 |
| EP | 0533511 A1 | 3/1993 |
| EP | 0655228 A1 | 5/1995 |
| EP | 0686379 A2 | 12/1995 |
| EP | 0696447 A2 | 2/1996 |
| EP | 0737450 A1 | 10/1996 |
| EP | 0743046 A1 | 11/1996 |
| EP | 0759287 A1 | 2/1997 |
| EP | 0771549 A2 | 5/1997 |
| EP | 0784988 A1 | 7/1997 |
| EP | 0852132 A1 | 7/1998 |
| EP | 0934729 A1 | 8/1999 |
| FR | 2580504 A1 | 10/1986 |
| FR | 2643250 A1 | 8/1990 |
| FR | 2666980 A1 | 3/1992 |
| FR | 2768326 A1 | 3/1999 |
| GB | 2020557 B | 1/1983 |
| GB | 2044109 B | 8/1983 |
| JP | 8187294 A | 7/1996 |
| SU | 764684 A1 | 9/1980 |
| WO | WO 9203097 A1 | 3/1992 |
| WO | WO 9414389 A1 | 7/1994 |
| WO | WO 9424946 A1 | 11/1994 |
| WO | WO 9601591 A1 | 1/1996 |
| WO | WO 9610375 A1 | 4/1996 |
| WO | WO 9619941 A1 | 7/1996 |
| WO | WO 9623441 A1 | 8/1996 |
| WO | WO 9633677 A1 | 10/1996 |
| WO | WO 9717100 A1 | 5/1997 |
| WO | WO 9727808 A1 | 8/1997 |
| WO | WO 9742879 A1 | 11/1997 |
| WO | WO 9802084 A2 | 1/1998 |
| WO | WO 9802112 A1 | 1/1998 |
| WO | WO 9823322 A1 | 6/1998 |
| WO | WO 9833443 A1 | 8/1998 |
| WO | WO 9834673 A1 | 8/1998 |
| WO | WO 9836786 A1 | 8/1998 |
| WO | WO 9838920 A1 | 9/1998 |
| WO | WO 9838929 A1 | 9/1998 |
| WO | WO 9839046 A1 | 9/1998 |
| WO | WO 9839053 A1 | 9/1998 |
| WO | WO 9846297 A1 | 10/1998 |
| WO | WO 9847447 A1 | 10/1998 |
| WO | WO 9849952 A1 | 11/1998 |
| WO | WO 9850103 A1 | 11/1998 |
| WO | WO 9851237 A1 | 11/1998 |
| WO | WO 9855175 A1 | 12/1998 |
| WO | WO 9909895 A1 | 3/1999 |
| WO | WO 9922673 A1 | 5/1999 |
| WO | WO 9923976 A1 | 5/1999 |
| WO | WO 9925252 A1 | 5/1999 |
| WO | WO 9930766 A1 | 6/1999 |
| WO | WO 9940964 A1 | 8/1999 |
| WO | WO 9942059 A2 | 8/1999 |
| WO | WO 9944510 A1 | 9/1999 |
| WO | WO 9944542 A2 | 9/1999 |
| WO | WO 9955236 A1 | 11/1999 |
| WO | WO 9958068 A2 | 11/1999 |
| WO | WO 0007655 A1 | 2/2000 |
| WO | WO 0009054 A1 | 2/2000 |
| WO | WO 0016705 A1 | 3/2000 |
| WO | WO 0049970 A1 | 8/2000 |

OTHER PUBLICATIONS

"Endovascular Grafts, Stents Drive Interventional Radiology Growth", Cardiovascular Device Update, 2(3):1-12, Mar. 1996.

Cragg et al., "A New Percutaneous Vena Cava Filger," AJR, 141:601-604, Sep. 1983.

(56) References Cited

OTHER PUBLICATIONS

Cragg et al., "Nonsurgical Placement of Arterial Endoprosthesis: A New Technique Using Nitinol Wire", AJR, 147(1):261-263, Apr. 1983.

Diethrich et al., "Percutaneous Techniques for Endoluminal Carotid Interventions", J. Endovasc. Surg., 3:182-202, 1996.

Fadali, "A Filtering Device for the Prevention of Particulate Embolization During the Course of Cardiac Surgery", Surgery, 64(3):634-639, Sep. 1968.

Haissaguerre et al., "Spontaneous Initiation of Atrial Fibrillation by Ectopic Beats Originating in the Pulmonary Veins", The New England Journal of Medicine, 339(10):659-666, Sep. 1988.

Jordan, Jr. et al., "Microemboli Detected by Transcranial Doppler Monitoring . . . ", Cardiovascular Surgery, 7(1)33-38, Jan. 1999.

Karalis et al., "Recognition and Embolic Potential of Intraaortic Atherosclerotic Debris", American College of Cardiology, 17(1):73-78, Jan. 1991.

Lesh, "Can Catheter Ablation Cure Atrial Fibrillation?", ACC Current Journal Review, p. 38-40, Sep./Oct. 1997.

Lund et al., "Long-Term Patentcy of Ductus Arteriosus After Balloon Dilation: An Experimental Study", Laboratory Investigation, 69(4):772-774, Apr. 1984.

Marache et al., "Percutaneous Transluminal Venous Angioplasty . . . ", American Heart Journal, 125(2 pt. 1):362-366, Feb. 1993.

Mazur et al., "Directional Atherectomy with the Omnicath™: A Unique New Catheter System", Catheterization and Cardiovascular Diagnosis, 31:17-84, 1994.

Moussa, MD, Issaam, "Stents Don't Require Systemic Anticoagulation . . . But the Technique (and results) Must be Optimal", Journal of Invasive Cardiol., 8(E):3E-7E, 1996.

Nakanishi et al., "Catheter Intervention to Venous System Using Expandable Metallic Stents", Rinsho Kyobu Geka, 14(2): English Abstract Only, Apr. 1994.

Onal et al., "Primary Stenting for Complex Atherosclerotic Plaques in Aortic and Iliac Stenoses", Cardiovascular & Interventional Radiology, 21(5):386-392, 1998.

Theron et al., "New Triple Coaxial Catheter System for Carotid Angioplasty with Cerebral Protection", American Journal of Neuroradiology, 11:869-874, 1990.

Tunick et al., "Protruding Atheromas in the Thoracic Aortic and Systematic Embolization", 115(6):423-427, American College of Physicians, 1991.

Tunick et al., "Protruding Atherosclerotic Plaque in the Aortic Archo F Patients with Systemic Embolization: A New Finding Seen by Transesophageal Echocardiography", American Heart Journal, 120(3):658-660, Sep. 1990.

Waksman et al., "Distal Embolization is Common After Directional Atherectomy . . . ," American Heart Journal, 129(3):430-435, 1995.

Wholey et al., PTA and Stents in the Treatment of Extracranial Circulation, The Journal of Invasive Cardiology, 8(E):25E-30E, 1996.

* cited by examiner

CATHETER WITH VARIABLE STIFFNESS

CROSS-REFERENCE TO RELATED APPLICATIONS

This application claims the benefit of U.S. Provisional Application Ser. No. 61/449,271, filed Mar. 4, 2011, the entire disclosure of which is incorporated herein by reference.

TECHNICAL FIELD

The present invention pertains to medical devices, and methods for manufacturing medical devices. More particularly, the present invention pertains to catheters that can vary in stiffness

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices. An example medical device may include an elongate inner member having a guidewire lumen extending therethrough. An outer member may be disposed about the inner member. An inflation lumen may be formed between the inner member and the outer member. The medical device may be configured to have a first stiffness when the inflation lumen is free of inflation media and a second stiffness different from the first stiffness when inflation media is disposed within the inflation lumen. In addition, the inner member may include a collapsible region that is configured to deflect radially inward when inflation media is disposed within the inflation lumen.

An example method for navigating a medical device through the vasculature may include providing a catheter. The catheter may include an elongate inner member having a guidewire lumen extending therethrough, an outer member disposed about the inner member, and an inflation lumen, which may be defined between the inner member and the outer member. The method may also include advancing a guidewire through the vasculature to a position adjacent to an area of interest, advancing the catheter over the guidewire, and infusing inflation media into the inflation lumen. Infusing inflation media into the inflation lumen may increase the stiffness of the catheter and it may deflect a portion of the inner member radially inward such that the inner member engages the guidewire.

An example variable stiffness catheter may include a catheter shaft. The catheter shaft may include an inner shaft and an outer shaft. A lumen may be formed between the inner shaft and the outer shaft. Infusion of a media into the lumen may increase the stiffness of the catheter shaft. Additionally, the inner shaft may have a collapsible region that is configured to deflect radially inward when media is infused into the lumen.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Figure 1:
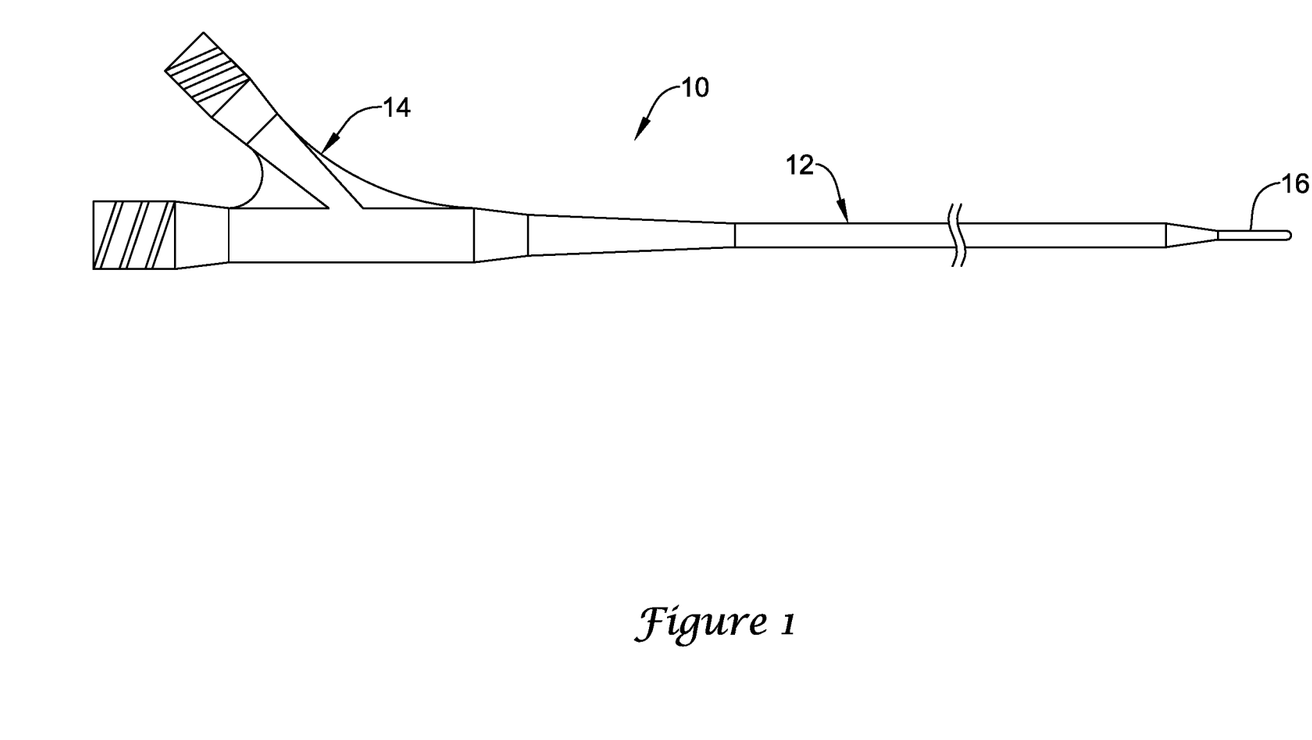
FIG. 1 is a side view of an example catheter disposed over a guidewire.

FIG. 1 is a side view of an example catheter 10. Catheter 10 may include a catheter shaft 12. A hub 14 may be coupled to the proximal end of catheter shaft 12. In general, catheter 10 may be a number of different interventions and may be configured to be advanced over or otherwise track over a guidewire 16. For example, catheter 10 may be a crossing catheter that is configured to cross tight lesions such as chronic total occlusions. This may include calcified lesions or occlusions. In addition or in the alternative, catheter 10 may be a guide catheter, a catheter for diagnosing and/or treating a medial condition, a delivery catheter (e.g., for stents, grafts, leads, or the like), or any other suitable medical device. In some embodiments, catheter 10 may include an inflatable balloon (not shown). In other embodiments, for example as shown, catheter 10 may be free of an expandable balloon. Indeed, catheter 10 may be thought of or take the form of a balloon catheter "without the balloon".

Figure 2:
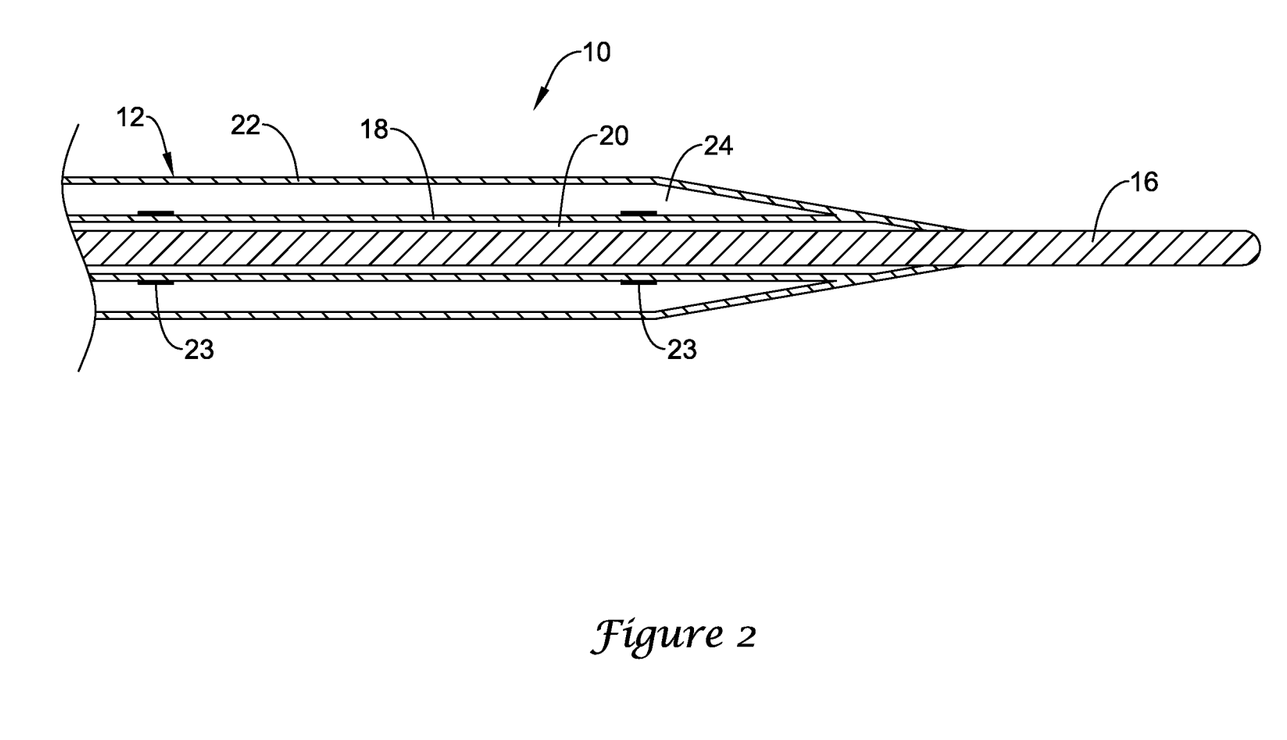
FIG. 2 is a cross-sectional side view of a portion of the example catheter and guidewire shown in FIG. 1.

FIG. 2 is a partial cross-sectional side view of a portion of catheter 10. Here it can be seen that catheter 10 (e.g., catheter shaft 12) includes an inner shaft or member 18. Inner shaft 18 may define a lumen 20 at least partially the length therethrough. In at least some embodiments, lumen 20 is a guidewire lumen. However, lumen 20 may also be an infusion and/or aspiration lumen. Other uses are also contemplated. In some embodiments, inner lumen 18 may include one or more additional lumens (not shown). Catheter shaft 12 may also include an outer shaft or member 22. Between inner shaft 18 and outer shaft 22, another lumen 24 may be defined. Lumen 24 may be thought of as an inflation lumen or otherwise may include a lumen into which media such as inflation media can be infused.

In the illustrated embodiment, inner shaft 18 is shown as having a length that is substantially the same as outer shaft 22. In other words, inner shaft 18 may extend along substantially the entire length of catheter shaft 12. Accordingly, guidewire lumen 20 may also extend along substantially the entire length of catheter 12 such that catheter 10 is an "over-the-wire" catheter. This, however, is not intended to be limiting as other catheters are contemplated where catheter 10 is a "single-operator-exchange" or "rapid-exchange" catheter, as these terms would be understood by one skilled in the art. In these embodiments, inner shaft 18 may extend along only a distal portion of outer shaft 22 and a port or opening (not shown) may be formed in the wall of outer shaft 22 that provides access to guidewire lumen 20.

Inner shaft 18 and outer shaft 22 may have a number of different configurations and/or material compositions. For example, inner shaft 18, outer shaft 22, or both may include one or more layers of material. In one example, inner shaft 18 may include three layers of material including an inner layer, and outer layer, and a tie layer disposed therebetween. In addition, inner shaft 18, outer shaft 22, or both may include a reinforcing structure such as a braid, mesh, coil, or other structure (not shown). This may provide catheter shaft 12 with improved strength.

One or more marker members or bands 23 may be disposed on inner shaft 18. Marker bands 23 may allow a clinician to more easily visualize catheter 10 under fluoroscopy or other visualization techniques (e.g., MRI, etc.). Because marker bands 23 are disposed on inner shaft 18 and because outer shaft 22 is also disposed about inner shaft 18, marker bands 23 may be covered or "encapsulated" within catheter shaft 12. Accordingly, marker bands 23 may be not exposed along the exterior of catheter shaft 12 where they might otherwise be susceptible to snagging or catching along the vasculature.

When using catheters (e.g., catheter 10) to gain access to lesions within the vasculature, it may be useful for the catheters to be highly flexible. This is because, for example, the vasculature may include a number of relatively sharp bends or take-offs. When navigating and/or treating the anatomy, it is possible that the catheter may encounter a lesion such as what is known as a chronic total occlusion. Such occlusion, which may be calcified or otherwise hardened, may be difficult to navigate through and/or treat, particularly with a highly flexible catheter.

Catheter 10 may be designed so as to have desirable flexibility characteristics so that it may be efficiently navigated through the anatomy (e.g., its flexibility may be comparable to that of catheters that are typically used to gain access to a variety of points within the vasculature). In addition, in order to more efficiently cross lesions such as a chronic total occlusions, catheter 10 may also have a variable flexibility or stiffness. Because of this, it may be possible for the clinician to alter the stiffness of catheter 10 (e.g., may provide "on demand" variability in stiffness) during a vascular intervention so that the flexibility and/or stiffness characteristics of catheter 10 can be tailored to the needs of the intervention. For example, catheter 10 may be configured to be relatively flexible so that it can efficiently navigate sharp bends or turns in the anatomy. In addition, catheter 10 may also be configured so that a clinician can increase the stiffness thereof, which may allow catheter 10 to be used to and/or aid in more efficiently crossing an occlusion such as a chronic total occlusion.

Figure 3:
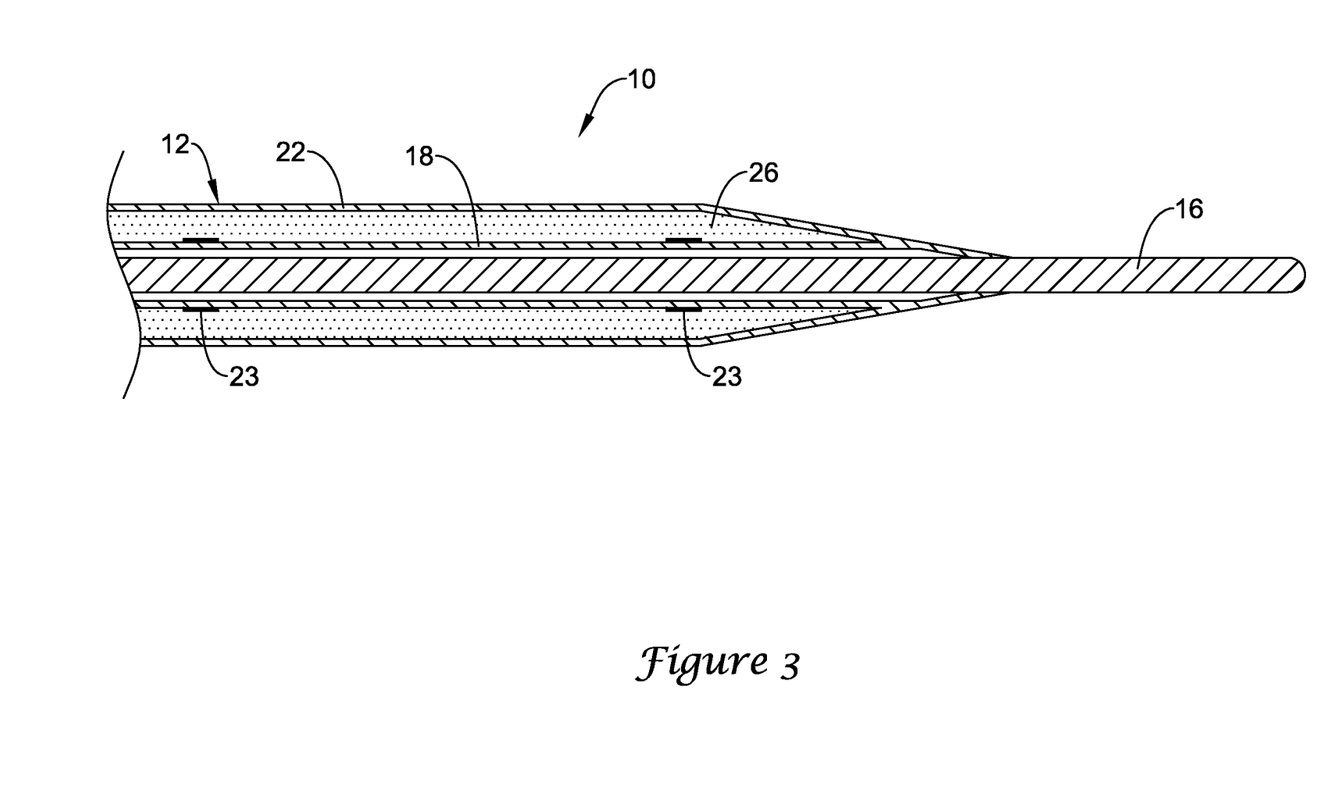
FIG. 3 is a cross-sectional side view of the example catheter and guidewire shown in FIGS. 1-2 with inflation media disposed therein.

In at least some embodiments, catheter 10 may be configured to have a varying stiffness through the infusion of media 26 for example inflation media, into lumen 24 as shown in FIG. 3 (note that lumen 24 is not labeled in FIGS. 3-5 due to the presence of media 26 but can be seen in FIG. 2). Media 24 may include any suitable media including a liquid or fluid (e.g., inflation media, saline, water, other fluids, etc.), a gas, colloidal materials, combinations thereof, and the like. In at least some embodiments, media 26 may be infused into lumen 24 using an inflation device such as those used commonly in the art. Other devices may also be used to infuse media 26 into lumen. The presence of the media 26 within lumen 24 may provide additional stiffness that may allow catheter 10 to have a greater ability to push through or otherwise past, for example, an occlusion. For example, when lumen 24 is substantially free of inflation media 26, catheter 10 may be sufficiently flexible so that it can navigate the anatomy. Infusing media 26 into lumen 24 may increase the stiffness of catheter 10, for example to hydraulic pressure exerted onto catheter shaft 12 by media 26. Indeed, the overall stiffness may be proportional to the amount of media 26 disposed in lumen 24. For example, a relatively small amount of media 26 (e.g., enough to fill lumen 24 but only exert a relatively small amount pressure onto inner shaft 18, outer shaft 22, or both) may increase the stiffness of catheter 10. This may include infusing sufficient media 26 into lumen 24 so that the total pressure within lumen 24 is in the range of about 0-4 pounds per square inch (PSI), or about 0-2 PSI, or about 2 PSI. Further infusion of media 26 (e.g., enough to pressurize lumen 24 such that increased force is applied to inner shaft 18, outer shaft 22, or both) may further stiffen catheter 10. This may include infusing sufficient media 26 into lumen 24 so that the total pressure within lumen 24 is in the range of about 2-16 PSI or more, or about 2-10 PSI or more, or about 2-8 PSI or more, or about 2-6 PSI or more. It can be appreciated that a large variety of stiffnesses can be achieved for catheter 10, depending on the quantity or "pressurization" of media 26 with lumen 24. While not wishing to be bound by theory, it is believed that once the pressure within lumen 24 reaches about 6 PSI, the stiffness begins to level off so that further infusion of media 26 may only alter the stiffness in relatively small increments.

It can be appreciated that in order to contain media 26, inner shaft 18 and outer shaft 22 may be attached, for example at their distal ends, and form a closed tip. The exact configuration of the tip can vary. For example, some embodiments may include a relatively gentle taper so as to provide catheter 10 with an atraumatic tip. Some of this and other embodiments may include an elongated tip or low profile tip, which may allow catheter 10 to probe deeper within the anatomy and within relatively narrow locations including the neurological vasculature.

Figure 4:
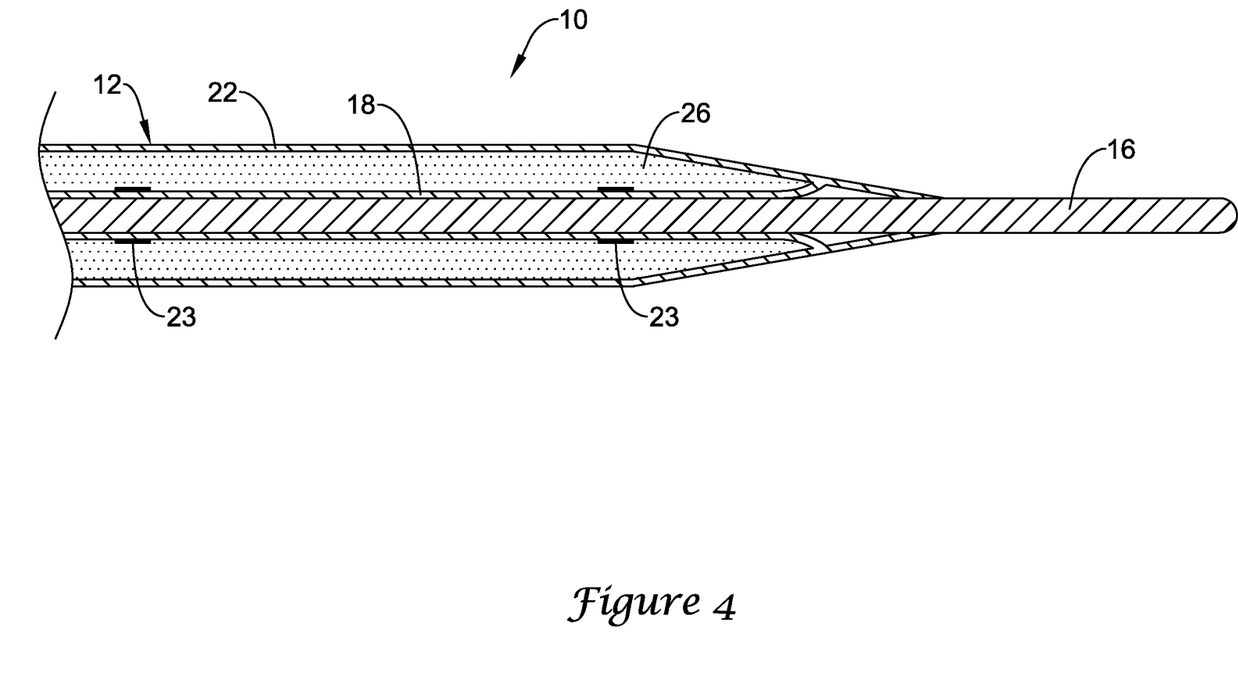
FIG. 4 is an alternative cross-sectional side view of the example catheter and guidewire shown in FIGS. 1-3 with inflation media disposed therein.

In addition to having a variable stiffness, inner member 18 may also be configured to deflect radially inward or otherwise collapse as shown in FIG. 4. In doing so, inner member 18 may exert force onto guidewire 16. This may be desirable for a number of reasons. For example, the deflection or collapse of inner shaft 18 may allow catheter 10 to grab onto or otherwise hold guidewire 16. This may allow a clinician to effectively move guidewire 16 in a predictable manner or otherwise provide greater control to the clinician of guidewire 16. In addition, by collapsing onto guidewire 16, catheter 10 may provide additional stiffness and/or pushability to guidewire 16, which may allow guidewire 16 to pass through some lesions and/or occlusions.

Figure 5:
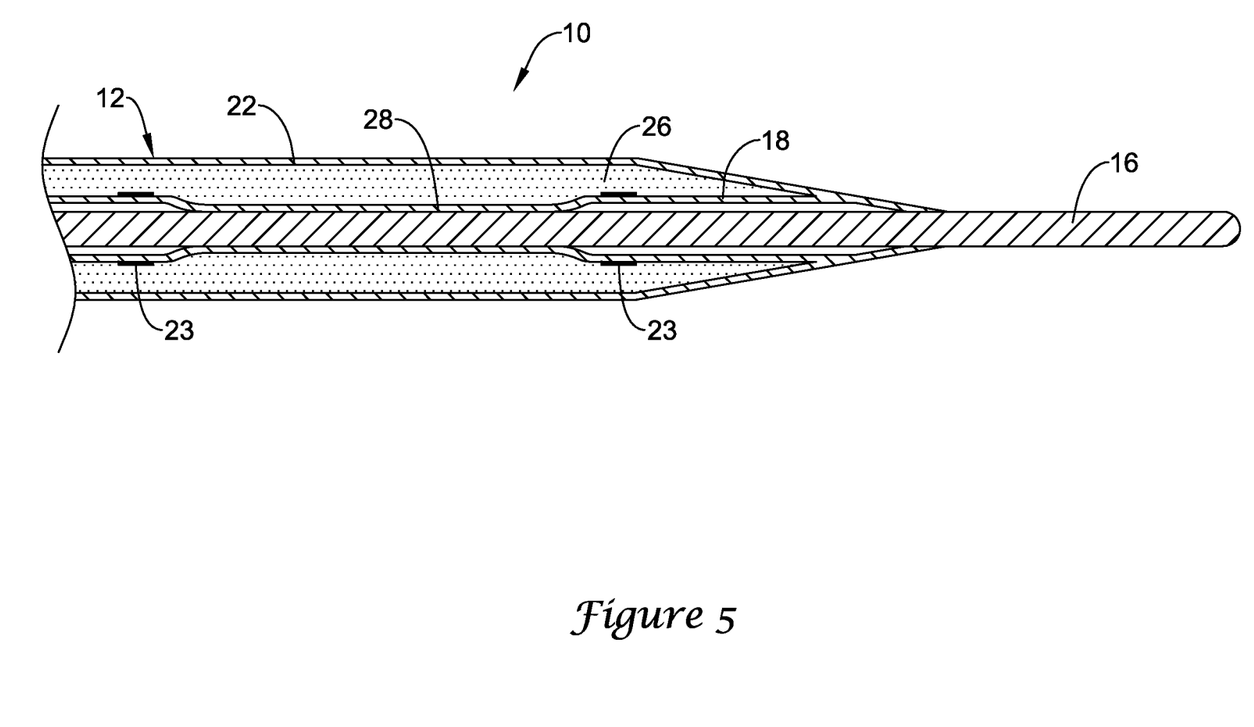
FIG. 5 is a cross-sectional side view of another example catheter and guidewire with inflation media disposed therein.

While FIG. 4 illustrates that in some instances, inner member 18 may be collapsible along substantially its entire length, other embodiments are contemplated where less than the full length of inner member 18 may collapse. For example, FIG. 5 illustrates catheter 10 where inner member 18 has a discrete section 28 that is configured to deflect radially inward or otherwise collapse when inflation media 26 is infused within lumen 24. In some embodiments, section 28 is defined during the manufacture of inner shaft 18 due to its shape, thickness, material composition, or other physical features. In other embodiments, inner member 18 may be simply collapsed at one or more discrete locations due to the positioning and/or location of catheter shaft 12 within the anatomy. It can be appreciated that some embodiments of inner shaft 18 include a plurality of discrete sections 28 (which may be spaced along the length of inner shaft 18) including two, three, four, five, six, seven, eight, nine, ten, or more sections 28. These are just examples.

Figure 6:
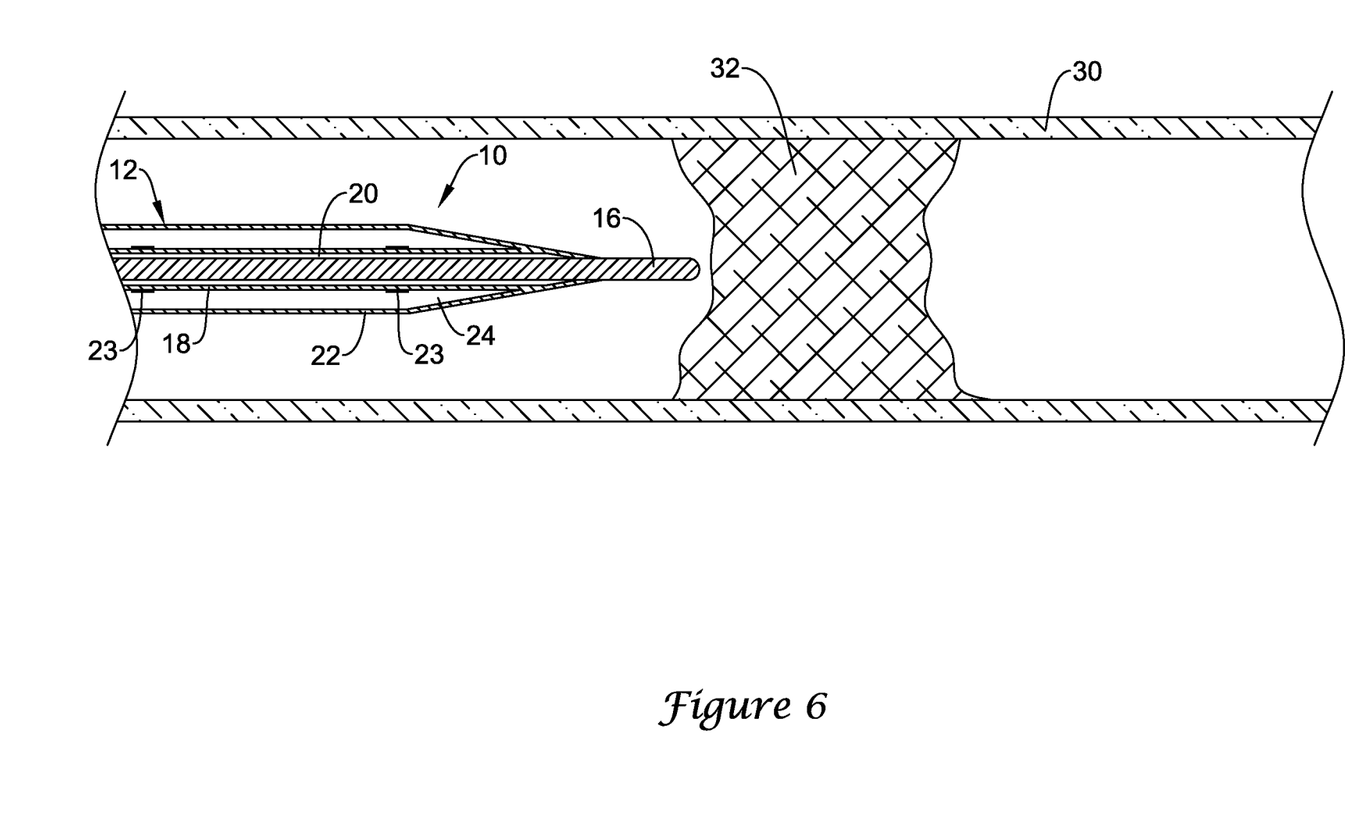
FIG. 6 is a cross-sectional side view of an example catheter disposed in a body lumen.
Figure 7:
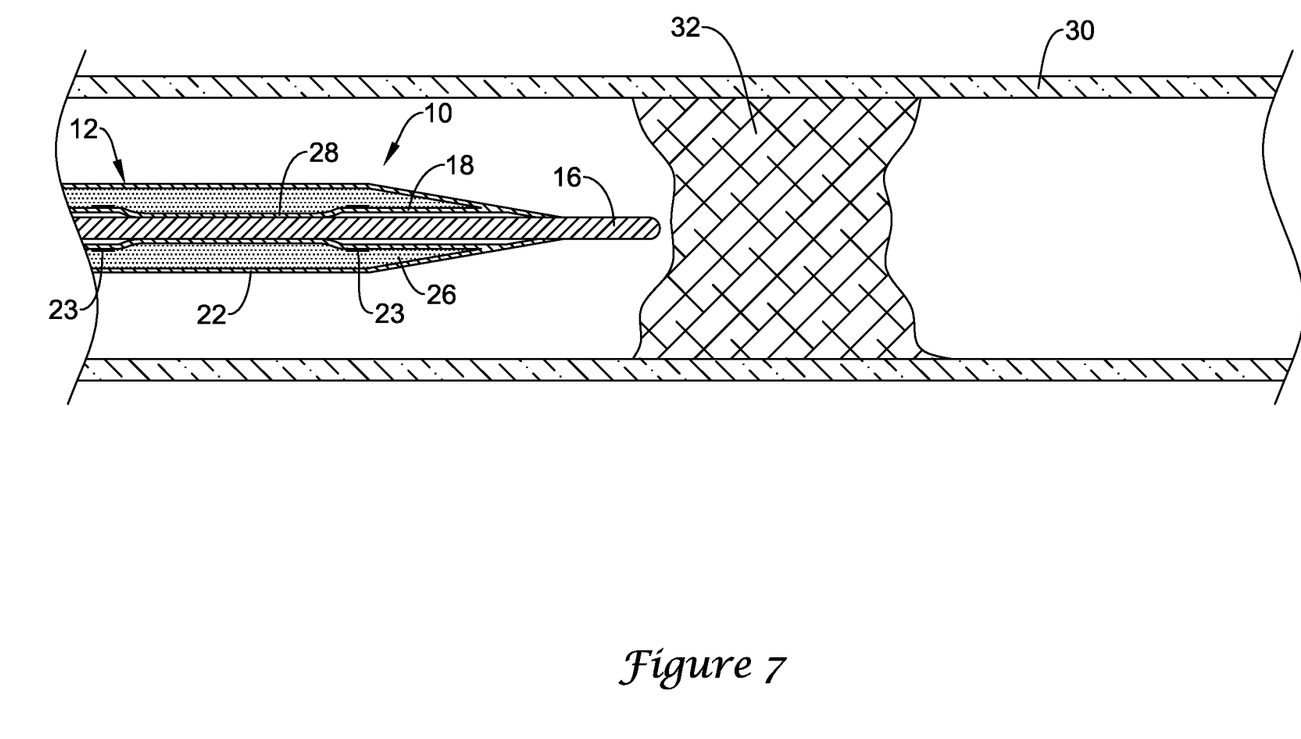
FIG. 7 is a cross-sectional side view of the example catheter shown in FIG. 6 with inflation media disposed therein.
Figure 8:
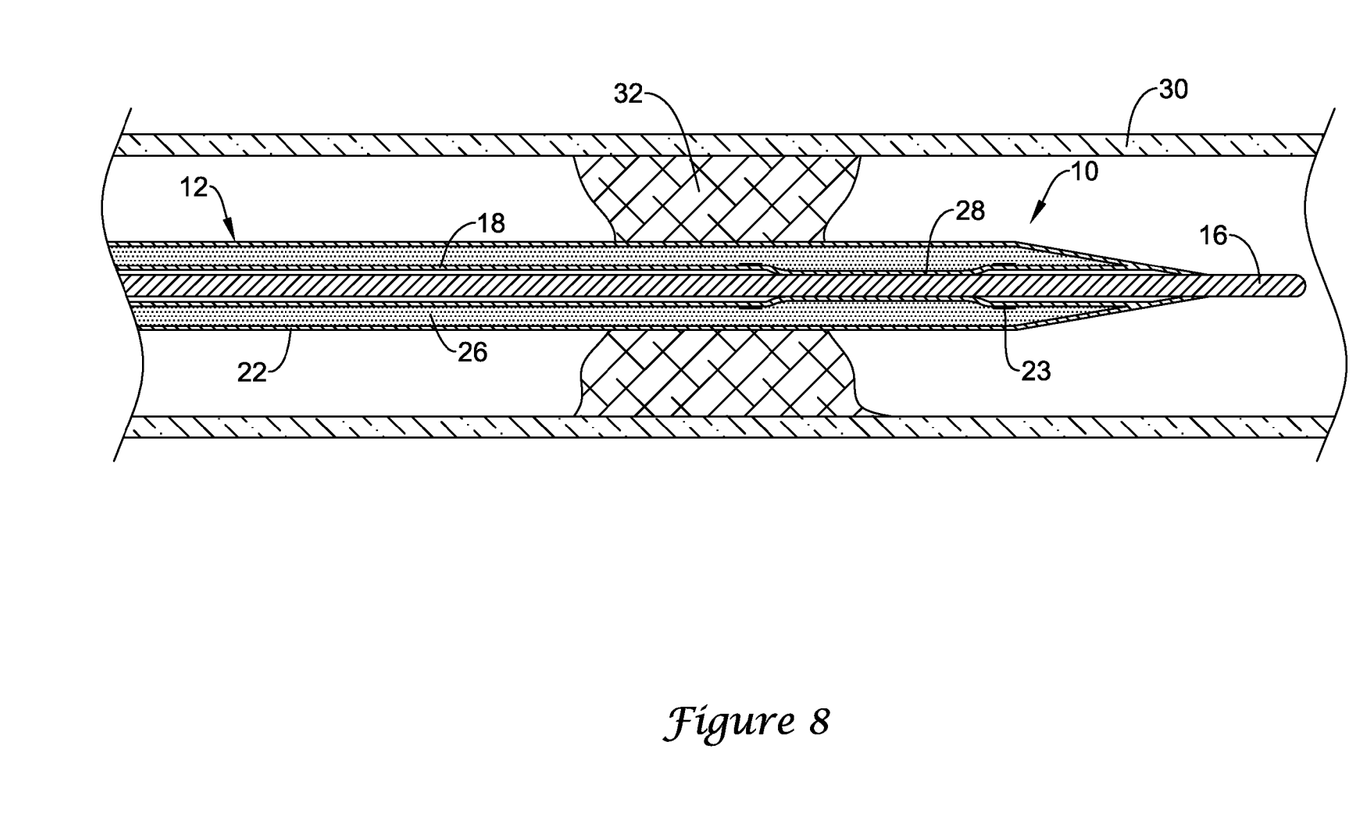
FIG. 8 is a cross-sectional side view of the example catheter shown in FIGS. 6-7 extending across a chronic total occlusion.

FIGS. 6-8 illustrate one example of some of the uses of catheter 10. For example, FIG. 6 illustrates catheter 10 advanced through a blood vessel 30 over guidewire 16 to a position adjacent to an occlusion 32. Upon reaching the occlusion, a number of steps may be taken to improve the possibility that catheter 10 can be advanced through occlusion 32. For example, a clinician may attempt to simply push or advance guidewire 16 and/or catheter 10 through occlusion 32. If not successful, guidewire 16 may be retracted and another guidewire, for example a stiffer guidewire, may be advanced through catheter 10 and another attempt to cross occlusion 32 may be made. In either instance, further attempts to cross occlusion 32 may be made with catheter 10 disposed about guidewire 16 or a different guidewire (e.g. while "supporting" guidewire 16). This may include supporting guidewire 16 by disposing catheter 10 (either pressurized or non-pressurized) adjacent to occlusion 32 while attempting to navigate guidewire 16 through occlusion 32. In addition, contrast media (not shown) can be passed through catheter 10 (e.g., through guidewire lumen 20) in order to better visualize occlusion 32. This may occur at any suitable time during the intervention.

Ultimately, it may be decided that additional pushability and/or stiffness may be necessary in order to cross occlusion 32. Accordingly, inflation media 26 may be infused into lumen 24 as shown in FIG. 7. This may provide additional stiffness to catheter 10 as described herein so that catheter 10 may be advanced through occlusion 32 as shown in FIG. 8. If initially pressurization is not sufficient to allow catheter 10 to cross occlusion 32, additional pressurization may be used (e.g., additional media 26 may be infused into catheter 10), which may further stiffen catheter 10, and further attempts may be made to cross occlusion 32. Some of these attempts may include pressurizing catheter 10 sufficiently to add stiffness to catheter 10 (which may or may not include collapsing inner shaft 18 onto guidewire 16), positioning catheter 10 adjacent to occlusion 32, and attempting to navigate guidewire 16 through occlusion 32 while catheter 10 supports guidewire 16. In addition, as described herein infusion of media 26 may also cause inner shaft 18 to collapse onto guidewire 16, which may provide additional support to guidewire 16 and/or allow the clinician to easily modify the position of guidewire 16 within the vessel 30. Once catheter 10 and guidewire 16 successfully cross occlusion 32, catheter 10 may be retracted and another treatment and/or diagnostic catheter or medical device may be passed over guidewire 16 and across occlusion 32.

Figure 9:
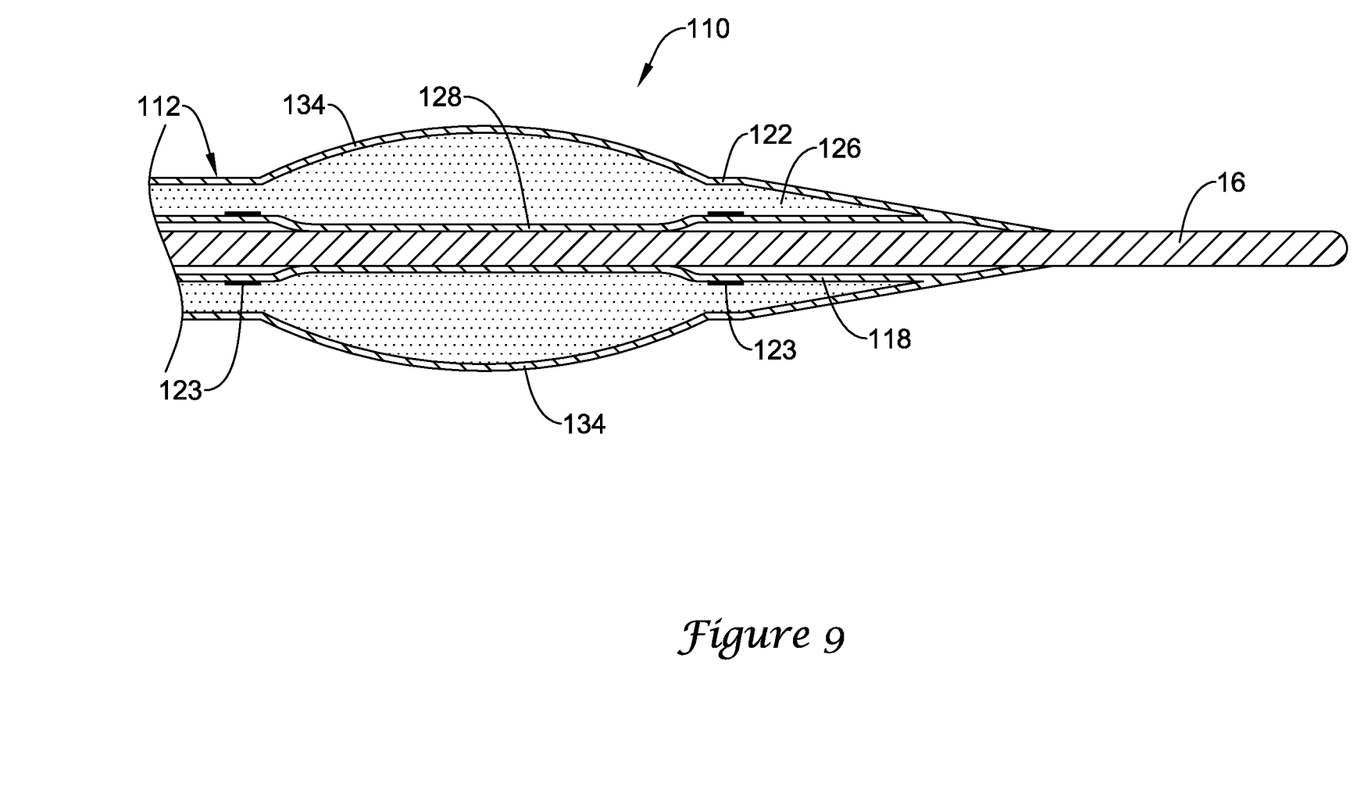
FIG. 9 is a cross-sectional side view of a portion of another example catheter.

FIG. 9 illustrates another example catheter 110 that may be similar in form and function to catheter 10. Catheter 110 includes catheter shaft 112 having inner shaft 118 and outer shaft 122. Marker bands 123 may be attached to inner shaft 118. Just like with catheter 10, inflation media 126 may be infused into the lumen (similar to lumen 24) formed between inner shaft 118 and outer shaft 122. In doing so, section 128 of inner shaft 118 may deflect radially inward and engage guidewire 16. In this example, section 128 is shown as a discrete section 128 of inner shaft 118. This, however, is not intended to be limiting as inner shaft 118 may also be configured to be collapsible along substantially its entire length.

Outer shaft 122 may include a deflectable portion 134. In this example, deflectable portion 134 is configured to deflect radially outward. In at least some embodiments, portion 134 may resemble a balloon or inflatable structure that deflects radially outward when inflation media 126 is infused into catheter 110. Deflection portion 134 may extend along only a discrete portion of outer shaft 122 (e.g., along a distal region), along multiple discrete portions of outer shaft 122, or along substantially the entire length of outer shaft 122. Deflectable portion 134 may be desirable for a number of reasons. For example, portion 134 may be used to expand or otherwise break up an occlusion (e.g., like occlusion 32) so that catheter 110 can be advanced through the occlusion. For example, catheter 110 may be advanced partially through or into an occlusion and deflectable portion 134 may be enlarged (e.g., deflected radially outward) to help break up the occlusion.

The materials that can be used for the various components of catheter 10 (and/or other catheters disclosed herein) and the various catheter shafts disclosed herein may include those commonly associated with medical devices. For simplicity purposes, the following discussion makes reference to catheter shaft 12 and other components of catheter 10. However, this is not intended to limit the devices and methods described herein, as the discussion may be applied to other similar tubular members and/or components of tubular members or devices disclosed herein.

Catheter shaft 12 and/or other components of catheter 10 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (°C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of catheter shaft 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of catheter 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of catheter 10 to achieve the same result.

In some embodiments, a degree of Magnetic Resonance Imaging (MRI) compatibility is imparted into catheter 10. For example, catheter shaft 12, or portions thereof, may be made of a material that does not substantially distort the image and create substantial artifacts (i.e., gaps in the image). Certain ferromagnetic materials, for example, may not be suitable because they may create artifacts in an MRI image. Catheter shaft 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of catheter shaft 12 that may define a generally smooth outer surface for catheter 10. In other embodiments, however, such a sheath or covering may be absent from a portion of all of catheter 10, such that catheter shaft 12 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the catheter 10 (including, for example, the exterior surface of catheter shaft 12) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of catheter shaft 12, or other portions of catheter 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device, comprising:
    an elongate inner member having a guidewire lumen extending therethrough;
    an outer member disposed about the inner member;
    wherein an inflation lumen is formed between the inner member and the outer member;
    wherein the medical device is configured to have a first stiffness when the inflation lumen is free of inflation media and a second stiffness different from the first stiffness when inflation media is disposed within the inflation lumen; and
    wherein the inner member includes a collapsible region that is configured to deflect radially inward when inflation media is disposed within the inflation lumen; and
    wherein the medical device is free of an expandable balloon.

2. The medical device of claim 1, wherein the inner member has a length and wherein the collapsible region extends along the entire length of the inner member.

3. The medical device of claim 1, wherein the inner member has a length and wherein the collapsible region extends along only a portion of the length of the inner member.

4. The medical device of claim 1, wherein the inner member further comprises one or more additional collapsible regions.

5. The medical device of claim 1, further comprising one or more marker members disposed along the inner member.

6. The medical device of claim 1, wherein the inner member has a distal end, wherein the outer member has a distal end, and wherein a sealed tip is formed between the distal end of the inner member and the distal end of the outer member.

7. The medical device of claim 1, wherein the inner member includes a plurality of layers.

8. A method for navigating a medical device through the vasculature, the method comprising:
    providing a catheter, the catheter comprising:
        an elongate inner member having a guidewire lumen extending therethrough,
        an outer member disposed about the inner member, and
        wherein an inflation lumen is defined between the inner member and the outer member and wherein the catheter is free of an expandable balloon;
    advancing a guidewire through the vasculature to a position adjacent to an area of interest;
    advancing the catheter over the guidewire;
    infusing inflation media into the inflation lumen;
    wherein infusing inflation media into the inflation lumen increases the stiffness of the catheter; and
    wherein infusing inflation media into the inflation lumen collapses a portion of the inner member radially inward along an entire length of the inner member such that the inner member engages the guidewire.

9. The method of claim 8, wherein the area of interest includes a chronic total occlusion and wherein advancing the catheter over the guidewire includes advancing the catheter to the chronic total occlusion.

10. The method of claim 8, wherein the catheter is free of an expandable balloon.

11. The method of claim 8, further comprising infusing contrast media through the guidewire lumen.

12. The method of claim 8, further comprising removing the guidewire from the guidewire lumen and advancing a second guidewire through the guidewire lumen.

13. A variable stiffness catheter, comprising:
a catheter shaft including an inner shaft and an outer shaft;
wherein a lumen is formed between the inner shaft and the outer shaft;
wherein infusion of a media into the lumen increases the stiffness of the catheter shaft;
wherein the inner shaft has a collapsible region extending an entire length of the inner shaft that is configured to deflect radially inward when media is infused into the lumen, and
wherein the catheter is free of an expandable balloon.

* * * * *

UNITED STATES PATENT AND TRADEMARK OFFICE
CERTIFICATE OF CORRECTION

PATENT NO.        : 8,821,478 B2
APPLICATION NO.   : 13/411309
DATED             : September 2, 2014
INVENTOR(S)       : Hanson et al.

It is certified that error appears in the above-identified patent and that said Letters Patent is hereby corrected as shown below:

In the Specification,

Column 7
Line 59: before ") to about 120°C", delete "."
Line 59: after "120°C", delete "."

Signed and Sealed this
Eighteenth Day of November, 2014

Michelle K. Lee
*Deputy Director of the United States Patent and Trademark Office*